United States Patent [19]

Bobichon et al.

[11] 4,438,784
[45] Mar. 27, 1984

[54] STOPPER FOR A SOURCE FOR AN X-RAY INSPECTION HOLE IN A PIPE OR OTHER APPARATUS

[75] Inventors: Jacques Bobichon, Verrières le Buisson; Pierre-Loup Leroy, Flines Lez Mortagne, both of France

[73] Assignee: Stein Industrie, Velizy-Villacoublay, France

[21] Appl. No.: 384,374

[22] Filed: Jun. 2, 1982

[30] Foreign Application Priority Data

Jun. 10, 1981 [FR] France ................ 81 11367

[51] Int. Cl.³ .................................. F16L 55/10
[52] U.S. Cl. ..................... 138/92; 220/284; 378/59
[58] Field of Search ......... 138/92, 89; 4/295, DIG. 7; 116/276; 220/359, 361, 284, 288; 215/302, 356; 378/59

[56] References Cited

U.S. PATENT DOCUMENTS

| | | | |
|---|---|---|---|
| 309,975 | 12/1884 | Nicolai | 138/89 |
| 1,208,355 | 12/1916 | Nechamkus | 220/359 |
| 1,690,183 | 11/1928 | Stoughton | 220/288 X |
| 2,310,351 | 2/1943 | Bowan et al. | 138/89 |
| 2,539,102 | 1/1951 | Rhoades | 378/59 |
| 3,412,759 | 11/1968 | Potter et al. | 138/89 |
| 3,412,886 | 11/1968 | Colella et al. | 215/215 |
| 3,451,432 | 6/1969 | Miller | 138/92 X |
| 3,814,276 | 6/1974 | Van Gordon et al. | 138/89 X |
| 4,153,067 | 5/1979 | Ray | 138/92 X |
| 4,344,460 | 8/1982 | Galos | 138/94 X |

FOREIGN PATENT DOCUMENTS 2308758 11/1976 France.

Primary Examiner—Stephen Marcus
Assistant Examiner—Mark Thronson
Attorney, Agent, or Firm—Sughrue, Mion, Zinn, Macpeak and Seas

[57] ABSTRACT

A stopper for an inspection hole to give an X-ray inspection probe access to the inside of a pipe or other apparatus wherein the stopper comprises a cylindrical outer component (6) having an open end and an inside screw thread (10), said outer component being welded to the wall (1) of said pipe or other apparatus and leaving an outside end protruding therefrom, and a cylindrical inner component (11) having a blind hole and an outside screw thread, said inner component being screwed into the inside screw thread of the outer component and having an outside end which is welded (12) around its periphery to the projecting outside end of the outer component, said blind hole being equipped with means (13) which allow the inner component to be unscrewed from the outer component after the weld (12) joining the outside ends of said components has been broken.

2 Claims, 1 Drawing Figure

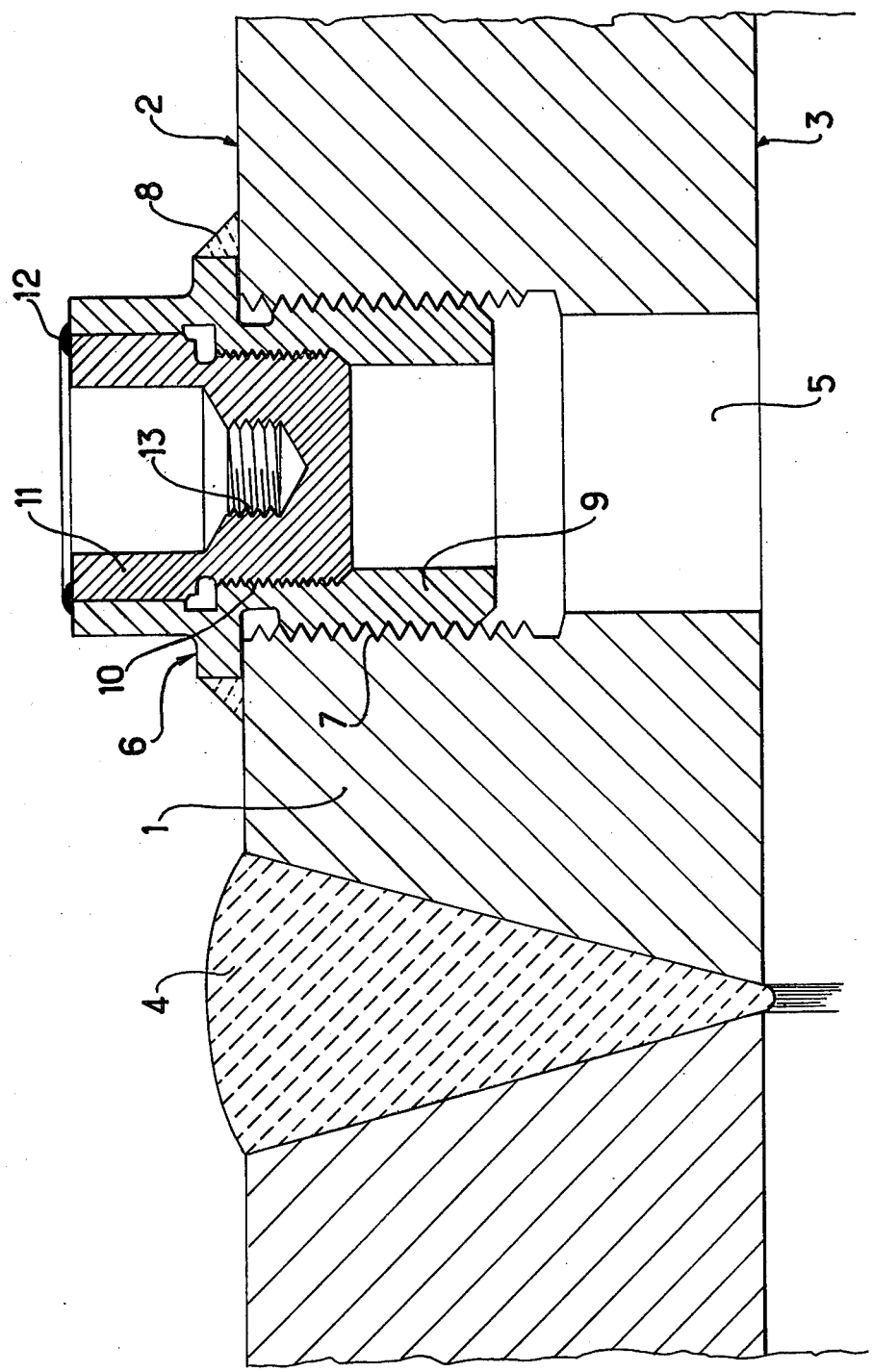

STOPPER FOR A SOURCE FOR AN X-RAY INSPECTION HOLE IN A PIPE OR OTHER APPARATUS

The present invention relates to an X-ray inspection probe access to the inside of a pipe or other apparatus in particular with a view to inspecting welds in the neighbourhood of said inspection hole.

BACKGROUND OF THE INVENTION

Known stoppers for holes via which X-ray inspection means are inserted into pipes, e.g., have closed ends and are welded onto the corresponding pipe or apparatus after X-ray inspection of the weld(s) to be inspected. They cannot be used again if welds need to be inspected at a later time after a given period of operation. The weld must be removed before unscrewing the stopper. This could damage the surface of the tube or apparatus to which the stopper is fitted. When further inspection is needed, another opening is therefore made in the wall, then said opening is closed after inspection by means of a new stopper which likewise cannot be used again. This is a relatively long and expensive operation and causes the wall to be successively pierced at points which are close to one another.

The present invention aims to remedy these drawbacks and to provide a stopper for such inspection openings which enable an X-ray source to be inserted inside a pipe or other apparatus as often as may be required and in a very short time.

The present invention provides a stopper for an inspection hole to give an X-ray inspection probe access to the inside of a pipe or other apparatus wherein the stopper comprises a cylindrical outer component having an open end and an inside screw thread, said outer component being welded to the wall of said pipe or other apparatus and leaving an outside end protruding therefrom, and a cylindrical inner component having a blind hole and an outside screw thread, said inner component being screwed into the inside screw thread of the outer component and having an outside end which is welded around its periphery to the projecting outside end of the outer component, said blind hole being equipped with means which allow the inner component to be unscrewed from the outer component after the weld joining the outside ends of said components has been broken.

Preferably, said means allowing the inner component to be unscrewed are constituted by an inside screw thread on said cylindrical inner component, the pitch of the screw thread being of the opposite hand to the pitch of its outside thread thereby enabling said second component to be unscrewed by means of a screw of matching pitch.

BRIEF DESCRIPTION OF THE DRAWING

A stopper for X-ray inspection of welds in a pipe in an electric power station is described hereinafter by way of example with reference to the sole FIGURE of the accompanying drawing, which is a cross-section through an inspection hole fitted with a stopper.

MORE DETAILED DESCRIPTION

The wall 1 of a pipe has an outside surface 2 and an inside surface 3. Said pipe has a weld bead 4 whose compactness needs to be checked periodically by X-ray means. For said purpose, the wall 1 has a cylindrical hole 5 through it. An outer stopper component 6 is fixed in the bore 7 of the hole 5, e.g. by screwing in a tapped hole. It is also fixed to the wall by circumferential welding 8. The bore 9 of the non-removable outer stopper component 6 is tapped at 10 to receive the outside thread of a removable inner stopper component 11. Said removable inner stopper component 11 is fixed to the non-removable outer stopper component 6 by a circumferential or peripheral weld 12. It also has a tapped blind hole with a left-handed thread 13 to which an extractor tool constituted by a screw with a left-handed thread can be fitted.

When successive X-ray checks need to be made, this is done as follows:

After fixing the outer stopper component 6 in the hole 5, the first X-ray inspection is made by inserting a probe into the pipe through the hole. Then the probe is removed, the outside thread of the removable inner stopper component 11 is lubricated with a grease that withstands high temperature (e.g. a graphite grease or a silicone grease) and said inner stopper component 11 is screwed into the non-removable outer stopper component 6. Then the edges of the two stopper components are welded together by the weld 12.

When a further inspection is needed, the circumferential weld 12 is removed preferably by grinding, since grinding is an operation which can be carried out very rapidly. A wrench with a left-handed thread which matches that of the inside thread 13 of the removable stopper component 11 is engaged in said thread, and then the removable stopper component 11 is unscrewed from the non-removable stopper component and is removed therefrom. The X-ray probe can then be inserted and the weld can be inspected.

After the X-ray inspection the probe is removed and the removable stopper component is screwed back into the non-removable stopper component and is then fixed in position by another weld. The operation can then be repeated many times.

Although the two-component stopper which has just been described with reference to the FIGURE of the drawing appears to be the preferred embodiment of the invention, it will be understood that various modifications can be made thereto without thereby going beyond the scope of the invention, it being possible to replace some of its components by others which could perform the same technical function. In particular, the left-handed thread of the removable stopper component and the corresponding wrench to remove said stopper could be replaced by any other means which allow an unscrewing force to be applied to said removable stopper component, e.g. a bayonet fitting.

We claim:

1. A stopper assembly for permitting inspection internally of a pipe or other apparatus by an X-ray inspection probe having access thereto, said stopper assembly comprising, in combination:
 - a hole within the wall of said pipe being threaded over at least a portion of its length from the outside of the pipe,
 - a cylindrical outer component having an external screw thread and being sized to and threadably engaging said threaded hole within said wall of said pipe,
 - said cylindrical outer component including an inside screw thread,
 - and said outer cylindrical component being threaded to said threaded hole within said wall of said pipe to an extent where a portion of said cylindrical outer component projects outside of said hole, said outer cylindrical component being welded to the outer surface of the wall of said pipe at an intermediate level where it projects outwardly from said hole, a cylindrical inner component having a blind hole, and having an outside screw thread sized to said outer cylindrical component inside screw thread, said inner component being screwed into the inside screw thread of the outer component to the extent such that its outside end is radially flush with the outside end of said outer cylindrical component, and a circumferential weld across the flush outside ends of the outer component and the inner component for fixedly joining the components, and wherein said blind hole is equipped with means for allowing the inner component to be unscrewed from the outer component after the weld joining the outside ends of said components is rapidly ground off;

whereby, a high strength, effectively sealed stopper assembly is provided, and wherein the inner component may be repeatedly screwed back into the outer cylindrical component, fixed with its end radially flush with the end of the outer component and fixed by another weld across the flush outside ends of said components and which weld also can be readily ground off to permit repetitive access internally of the pipe by said X-ray inspection probe.

2. A stopper according to claim 1, wherein the means allowing the inner component to be unscrewed are constituted by an inside screw thread on said cylindrical inner component, the pitch of said screw thread being of the opposite hand to the pitch of the outside thread on said inner component.

* * * * *